(12) United States Patent
Henderson et al.

(10) Patent No.: US 10,154,822 B2
(45) Date of Patent: Dec. 18, 2018

(54) PATIENT POSITIONER SYSTEM

(71) Applicants: Toby D. Henderson, Rockford, IL (US); Niek Schreuder, Bloomington, IN (US); Brian Broderick, Bloomington, IN (US)

(72) Inventors: Toby D. Henderson, Rockford, IL (US); Niek Schreuder, Bloomington, IN (US); Brian Broderick, Bloomington, IN (US)

( * ) Notice: Subject to any disclaimer, the term of this patent is extended or adjusted under 35 U.S.C. 154(b) by 104 days.

(21) Appl. No.: 14/951,235

(22) Filed: Nov. 24, 2015

(65) Prior Publication Data

US 2016/0073978 A1    Mar. 17, 2016

Related U.S. Application Data

(63) Continuation of application No. 12/208,807, filed on Sep. 11, 2008, now Pat. No. 9,199,372.

(Continued)

(51) Int. Cl.
*G05B 13/02*    (2006.01)
*A61B 6/04*    (2006.01)
(Continued)

(52) U.S. Cl.
CPC .......... *A61B 6/0457* (2013.01); *A61N 5/1049* (2013.01); *B25J 9/042* (2013.01);
(Continued)

(58) Field of Classification Search
CPC ...... A61B 6/0457; A61N 5/1049; B25J 9/042; B25J 5/0019; B25J 9/1689; B25J 9/1676;
(Continued)

(56) References Cited

U.S. PATENT DOCUMENTS 4,906,123 A    3/1990  Weskamp et al.
5,046,495 A    9/1991  Takahashi et al.
(Continued)

FOREIGN PATENT DOCUMENTS

JP           11077566 A      3/1999
KR   10 2006 0135063 A     12/2006
(Continued)

OTHER PUBLICATIONS

Anferov et al.; The expected radiation failure rate for optical encoders used in the MPRI patient positioner; (presentation) Particle Therapy Co-Operative Group Meeting—Catania, Italy; 11 pgs.; May 27-31, 2002.

(Continued)

*Primary Examiner* — Bhavesh V Amin
(74) *Attorney, Agent, or Firm* — Hamilton IP Law, PC; Jay R. Hamilton; Charles Damschen

(57) ABSTRACT

A computer controlled robot system for positioning a patient for radiation therapy or other medical procedures and the like. The robot is mounted at the top of a vertical shaft extending from the treatment room floor and includes horizontal arms arranged to maximize the available work envelope and eliminate "dead spots" in the envelope that the robot cannot reach. A double redundant coupling system for coupling devices to the robot is provided. A vision based docking system is employed for automatically coupling devices to the robot. Various enhanced safety features are provided, including device specific collision avoidance.

26 Claims, 8 Drawing Sheets

Related U.S. Application Data

(60) Provisional application No. 60/972,107, filed on Sep. 13, 2007.

(51) Int. Cl.

| | | |
|---|---|---|
| *A61N 5/10* | (2006.01) | |
| *B25J 9/04* | (2006.01) | |
| *B25J 9/16* | (2006.01) | |
| *B25J 15/00* | (2006.01) | |

(52) U.S. Cl.
CPC ........... *B25J 9/1671* (2013.01); *B25J 9/1674* (2013.01); *B25J 9/1676* (2013.01); *B25J 9/1689* (2013.01); *B25J 15/0019* (2013.01); *A61N 2005/1087* (2013.01); *Y10S 901/02* (2013.01); *Y10S 901/09* (2013.01); *Y10S 901/11* (2013.01)

(58) Field of Classification Search
CPC ..... B25J 9/1674; B25J 9/1671; Y10S 901/09; Y10S 901/11
See application file for complete search history.

(56) References Cited

U.S. PATENT DOCUMENTS

| | | | |
|---|---|---|---|
| 5,204,598 A | | 4/1993 | Torii et al. |
| 5,243,264 A | | 9/1993 | Takada et al. |
| 5,280,622 A | | 1/1994 | Tino |
| 5,321,271 A | | 6/1994 | Schonberg et al. |
| 5,341,459 A | | 8/1994 | Backes |
| 5,410,767 A | | 5/1995 | Barud |
| 5,428,279 A | * | 6/1995 | Sugimoto ................ B25J 19/06 318/445 |
| 5,540,649 A | | 7/1996 | Bonnell et al. |
| 5,548,625 A | | 8/1996 | Waldo, III |
| 5,727,554 A | | 3/1998 | Kalend et al. |
| 5,784,431 A | | 7/1998 | Kalend et al. |
| 5,903,123 A | * | 5/1999 | Shimogama ........... B25J 9/1674 318/563 |
| 5,944,476 A | | 8/1999 | Bacchi et al. |
| 6,019,563 A | * | 2/2000 | Murata ................ B23Q 7/1436 414/222.01 |
| 6,094,760 A | | 8/2000 | Nonaka et al. |
| 6,126,381 A | | 10/2000 | Bacchi et al. |
| 6,155,768 A | | 12/2000 | Bacchi et al. |
| 6,275,748 B1 | | 8/2001 | Bacchi et al. |
| 6,811,313 B2 | | 11/2004 | Graumann et al. |
| 6,869,217 B2 | | 3/2005 | Rasche et al. |
| 6,902,015 B2 | * | 6/2005 | Furuta .................... B25J 13/081 180/8.6 |
| 7,154,991 B2 | | 12/2006 | Earnst et al. |
| 7,300,205 B2 | | 11/2007 | Grady |
| 7,610,115 B2 | | 10/2009 | Rob et al. |
| 7,813,838 B2 | | 10/2010 | Sommer |
| 9,199,372 B2 | | 12/2015 | Henderson et al. |
| 2002/0192056 A1 | | 12/2002 | Reimer et al. |
| 2003/0035711 A1 | * | 2/2003 | Gilchrist ........... H01L 21/68707 414/744.5 |
| 2003/0198376 A1 | * | 10/2003 | Sadighi ................ B25J 9/1697 382/153 |
| 2004/0064153 A1 | | 4/2004 | Creighton, IV et al. |
| 2004/0184579 A1 | | 9/2004 | Mihara et al. |
| 2005/0187424 A1 | | 8/2005 | Hambuchen et al. |
| 2005/0194540 A1 | | 9/2005 | Fenster et al. |
| 2005/0234327 A1 | * | 10/2005 | Saracen ............... A61B 6/0457 600/407 |
| 2006/0050847 A1 | | 3/2006 | Jaffray et al. |
| 2007/0135703 A1 | * | 6/2007 | Rietzel .................... A61B 6/04 600/407 |
| 2007/0230660 A1 | | 10/2007 | Herrmann |
| 2008/0235970 A1 | * | 10/2008 | Crampton .............. B25J 13/088 33/503 |
| 2009/0070936 A1 | * | 3/2009 | Henderson ........... A61B 6/0457 5/601 |

FOREIGN PATENT DOCUMENTS

| | | |
|---|---|---|
| KR | 100695468 B1 | 3/2007 |
| WO | WO 2006/034973 A1 | 4/2006 |

OTHER PUBLICATIONS

Kats et al.; A planar magnetooptical system for the irradiation of a lying patient with a proton beam from various directions; Instruments and Experimental Techniques; vol. 39; No. 1; pp. 127-134; 1996.

Kats, M.; Planar system replacing gantry for protons and carbon ions beams transportation; Proceedings of the 6th European Particle Accelerator Conference (EPAC'98); pp. 2362-2364, 1998.

Katuin et al.; The use of industrial robot arms for high precision patient positioning; CAARI; 4 pgs.; 2002.

Schreuder et al.; Beam delivery developments; (presentation) Particle Therapy Co-Operative Group Meeting; 20 pgs.; May 14, 2003.

Schreuder et al.; IGRT methods used in patient positioning; (presentation) ORVC Fall 2005 Meeting; Indiana Univ. Cyclotron facility—Bloomington, Indiana; 26 pgs.; Nov. 5, 2005.

Schreuder et al.; MPRI operational aspects; (presentation) Particle Therapy Co-Operative Group Meeting—Bloomington, Indiana; 24 pgs.; Oct. 10-13, 2004.

Schreuder et al.; The MPRI robotic patient positioner; (presentation) Particle Therapy Co-Operative Group Meeting—Paris; 14 pgs.; Jun. 16, 2004.

Schreuder et al.; The non-orthogonal fixed beam arrangement for the second proton therapy facility at the national accelerator centre; CAARI; 4 pgs.; 1998.

Schreuder et al.; Using industrial robots for high precision patient positioning in proton radiotherapy; (presentation) RIA—Orlando, Florida; 48 pgs.; Nov. 19, 2004.

* cited by examiner

PATIENT POSITIONER SYSTEM

CROSS-REFERENCE TO RELATED PATENT APPLICATIONS

This patent application is a continuation of U.S. patent application Ser. No. 12/208,807, filed Sep. 11, 2008, which is now pending, and which claims the benefit of U.S. Provisional Patent Application No. 60/972,107, filed Sep. 13, 2007, the entire teachings and disclosure of which are incorporated herein by reference thereto.

FIELD OF THE INVENTION

This invention pertains generally to robotics and more particularly to robotic systems for positioning patients for medical procedures.

BACKGROUND OF THE INVENTION

Robots used in industrial manufacturing applications are well known. Such robots are designed and programmed to perform specific functions repeatedly and precisely. Thus, robots are often used in such applications to perform operations, such as assembly in an assembly line setting, more efficiently, and often producing higher and more consistent quality, than such operations could be performed by humans.

Conventional industrial robots typically have one or two robotic arms. These robotic arms can have multiple segments that facilitate movement in multiple degrees of freedom (DOF). Movement of the arms may be provided by stepper or other controllable motors, typically under computer control. In other applications hydraulics or pneumatics may be used to actuate the robot arm segments.

An example of a typical industrial robot is a Selectively Compliant Articulated Robot Arm (SCARA) robot. Known SCARA robots typically operate with four or fewer degrees of freedom, i.e., these robots are designed to move along four or fewer axes of rotation.

A typical application for a conventional robotic arm of this type in an industrial setting is that of a pick-and-place type machine. Pick-and-place type machines are used for automation assembly, automation placing, printed circuit board manufacturing, integrated circuit pick and placing, and other automation jobs that contain small items, such as machining, measuring, testing, and welding. These robotic arms include an end-effector, also known as a robotic peripheral, robotic accessory, robot or robotic tool, end of arm (EOA) tooling, or end-of-arm device. The end effector may be implemented such as a robotic gripper, press tool, paint gun, blowtorch, debarring tool, arc welding gun, drills, etc. These end-effectors are typically placed at the end of the robotic arm and are used to perform the functions described above. One common end-effector is a simplified robotic version of a hand, which can grasp and carry different objects.

Some conventional industrial robots have been modified for patient positioning in a medical setting. For example, in external radio therapy, e.g., using a proton beam, the radiation beam employed is either fixed or of limited mobility. In such an application a patient may be positioned on a patient treatment table that in turn is coupled to the end of the robot arm. The robot is then precisely controlled to move the patient relative to the treatment beam to achieve the desired therapeutic exposure. Precise control is achieved in such an application by the precise positioning of the patient on the treatment table such that the exact position of the treatment area of the patient, obtained prior to therapy, is known with respect to the position of the robot arm at any point in time.

An example of a robot used in such a medical setting is described in United States Patent Application Publication No. US 2005/0234327, entitled "Robotic Arm for Patient Positioning Assembly". This robotic patient positioning assembly includes an articulated robot arm that includes a track mount assembly to facilitate movement of a patient on a patient treatment couch (e.g., table or chair) in a three dimensional (3D) space, as well as raising and lowering the patient to high and low positions without compromising the flexibility or positioning in translational and rotational movements. The track mount assembly may be vertically mounted, for example to a vertical side of a column. This particular system features a first arm segment movably attached at a first end thereof to the track mount assembly that is attached to the vertical column, and a second arm segment, of different length from the first arm segment, moveably attached at a first end thereof to the second end of the first arm segment. The patient table is positioned at the second end of the second arm segment. The second arm segment is attached below the first arm segment, such that the patient table may be lowered as close to the floor of the treatment room as possible. Unfortunately, this arrangement provides an envelope in which the patient table may be positioned that has voids. In other words, by having the second arm below the first, the second arm runs into the track mount assembly.

This limited positioning envelope 300 is illustrated in FIG. 8. More particularly, second arm segment 302 is positioned below first arm segment 304 that is mounted to track mount assembly 306. Thus, the motion of the second arm segment 302, and typically even the first arm segment 304, is obstructed by the track mount assembly 306. Thus, the envelope 300 is created that limits the positioning of any device, typically the patient table, mounted to the end of the robotic arm. These limitations may be referred to as "dead spots" illustrated generally at 308.

Further, as illustrated in U.S. Patent Application Publication 2007/0230660 published Oct. 4, 2007 entitled "Medical Radiotherapy Assembly," to Herrmann, a robotic patient positioner system is illustrated. However, in this robotic system the vertical movement is not provided in a direct perpendicular path relative the floor. Instead, two robotic arms must be moved relative to one another to get a variation in the vertical position of the patient. Further, due to the lack of a direct linear vertical positioning component, the envelope for positioning the patient is limited. This arrangement provides for numerous dead spots within the envelope for positioning the patient relative to the particle emitter therefore limiting the effectiveness of the patient positioner system.

The use of robots for patient positioning in medical treatment and similar settings poses both opportunities for increased patient treatment efficiency (and therefore lower cost) and effectiveness, and challenges for patient and medical personnel safety. Radiotherapy operations, such as proton beam treatment, can be very expensive, both in the capital cost involved in setting up such a facility and the operational costs associated with facility operations. To the extent that patient positioning system robots can be used to reduce overall treatment facility capital costs and/or increase patient throughput, that is, reduce the time required for each patient to occupy the facility to receive the desired treatment, the per patient treatment costs can be reduced. However, such increased efficiency can not be obtained at the cost of reduced treatment effectiveness or of reduced safety to the patient or to medical personnel providing such treatment. What is desired, therefore, is an improved patient positioning system that takes advantage of robot technology to the greatest extent to improve the efficiency (reduce the cost of) and effectiveness of patient radio therapy and other treatments while improving patient and operator safety as well.

BRIEF SUMMARY OF THE INVENTION

The present invention provides an improved patient positioner system for radiotherapy and other medical applications. The present invention features a patient positioning robot under computer control that is designed and controlled in manner so as to reduce overall treatment facility capital costs, increase patient throughput, thereby reducing operational costs, while simultaneously increasing patient and treatment facility operator safety.

The present invention features a computer controlled robot providing five degrees of rotational freedom and a linear degree of freedom in the vertical direction. The robot includes a first arm segment that is moveably attached at a first end thereof to the top of a vertical shaft that operates from a pit underneath the floor of the treatment room. The vertical shaft may be elevated and lowered to raise or lower the position of the patient table in the treatment room. The first robot arm extends horizontally from the vertical shaft and is rotatable in a complete circle in the horizontal direction about the vertical shaft. A second robot arm segment is moveably attached at a first end thereof to the second end of the first robot arm segment. The second robot arm segment is preferably of the same length as the first robot arm segment and is attached to the first arm segment to extend parallel thereto such that the second arm segment is rotatable in a complete circle in a horizontal direction about the joint between the arm segments, such that the second arm segment passes over the first arm segment. A robotic wrist assembly is attached at the second end of the second arm segment, extending generally upward therefrom so as not to interfere with rotation of the second arm segment with respect to the first arm segment. The patient table is attached to the wrist assembly. The wrist assembly provides for three axes of rotation (pitch, roll, and yaw) of the patient table with respect to the second end of the second arm segment.

Due to the unique arrangement of the horizontal arm segments and the vertical shaft operating from the floor a patient may be positioned anywhere in a complete circle within the reach of the robot arm segments. Not only is the work envelope increased in size, but the arrangement of the robot arm segments provides a more functional work envelope by allowing for the robot wrist to reach any point in the envelope. This means that there are no "dead spots" in the envelope. It also allows for easy movement and collision free trajectories inside the work envelope. The easier motion trajectories allows for easy restrictions to the allowed envelope through standard firmware parameters. This is an advantage over previous robotic patient positioning systems in which the use of a vertical column to mount the system and the relative position of the robot arm segments reduces and restricts the available work envelope and freedom of arm movement trajectories.

The patient positioner system in accordance with the present invention preferably is designed to eliminate wires, cables, and the like hanging from the robot arm segments. This improves the appearance, safety, and functionality of the system. To achieve this desired result the present invention preferably employs gear boxes connecting the first arm segment to the vertical shaft and between the first and second robot arm segments that include through holes or other apertures formed therein. This allows the necessary control cables to be run to the end of the second robot arm segment through, rather than outside of, the gear boxes. The arm segments may then be provided with covers, with the control cables and wires contained entirely therein along the length of the arm segments.

The gear boxes employed in the patient positioner system of the present invention preferably feature double gear reduction, to limit maximum rotation speed. This limits the speed of robot arm movement in the unlikely event of an out-of-control run away situation, thereby giving an operator an opportunity to hit an emergency kill switch to shut down the system.

A patient positioner system in accordance with the present invention features an absence of any moving parts in the floor system. Since only a vertical shaft protrudes from the floor of the room a stationary floor covering system may be employed. This makes the use and installation of the system much easier and allows for easier adaptation to the users needs.

The present invention preferably also features a uniquely designed dual coupler system that may be used to attach patient positioning devices (e.g., a patient table) and quality assurance devices (e.g., test phantoms) to the wrist end of the robot system. Two independent couplers are provided, each coupler on its own being sufficient to provide the safe and secure attachment required. Each coupler is individually controlled through independent control circuits. This provides a double redundant safe coupling system. The dual coupler design allows for more space efficient implementation of the coupler system.

A load cell may preferably be positioned between the mating flange on a patient table, for example, and the robot flange. For example a six point piezoelectric strain gauge or similar structure may be used for this purpose. Such a device can be used as a safety measure to detect forces at the end of the robot arm that may indicate, for example, that the patient position on the table is shifting, and there is a danger of a fall. These movements of the table due to shifting, would result in misalignment of the tumor sight. Alternatively, such a structure may be used to determine patient weight or the like.

In an embodiment, the system may be able to adjust pitch and roll about axes to adjust the position of the table or couch from horizontal. This ability to adjust the pitch and roll provides greater degrees of angular treatment. As an additional safety feature of the present invention, the arrangement of the robot arms allows for the mechanical restriction of the range of motion of the pitch and roll axes of rotation. Thus, rotations out of the horizontal planes can be restricted to a desired absolute maximum, e.g., +/−15 degrees. This reduces the likelihood that a patient is tipped off of a patient table, or made to feel uncomfortable of such a result by excessive tipping of the patient table.

The patient positioning system robot of the present invention is under computer control. In accordance with the present invention, control of the patient position system robot is also implemented to increase treatment efficiency, effectiveness, and safety.

One form of the computer control that may be used is the KUKA Safe Robot technology. This KUKA Safe Robot control technology controls the robot safely without mechanical axis range monitoring. The control software functions to prevent the robot from "breaking out" of its defined workspace. More particularly, the robot control monitors the velocity and acceleration of the robot components about a given axis to prevent "breaking out."

The patient positioning system of the present invention features a device specific collision avoidance algorithm. As in conventional robot control systems, sensors are used to monitor the position in real space of specific points on the robot, e.g., the end of the robot arm near the wrist assembly. In addition to this positional feedback information for specific points on the robot, the present invention may employ computer aided design (CAD) representations of the entire robot structure surface, as well as of any device attached to the robot, e.g., a patient table, to determine the position in the work space of the surface of the entire system. Thus, the collision avoidance algorithm may be specific for each device attached to the patient positioner system. In this manner the robot may be operated so as to avoid collisions between any parts of the system itself, or between the system and any other structures where the position of such structures is provided to the system.

The present invention preferably employs a vision based docking system to facilitate the docking of different devices to the system. The docking system employs a vision camera or other optical detection device mounted in an appropriate place in the treatment room within the work envelope of the robot, e.g., the camera may be mounted in the floor of the treatment room. Devices to be mounted to the positioner system (e.g., patients already positioned on tables, test phantoms, etc.) are positioned on support carts in the room in the field of view of the camera. The support cart need only be in a certain approximate location for the camera to pick up the location of the device to be mounted on the system. Markings or other indices on the support cart are detected by the camera, thereby allowing the computer control system to detect the position of the cart that carries the device considered for docking or un-docking. Bar code technology and alignment marks on the device and/or the cart allow the system to identify the particular device to be attached to the robot and to automatically manipulate the robot arm into the desired position to automatically attach the device to the robot. This automated docking system increases the efficiency with which a treatment facility may be used, e.g., by reducing the time required to attach a patient to the system, and obviates the need for rigid docking fixtures in the floor of the treatment room.

As an additional safety feature, a patient positioner system in accordance with the present invention preferably is equipped with a plurality (e.g., three) auxiliary disturbance circuits. The auxiliary disturbance circuits allow for the seamless addition of auxiliary disturbance switches and circuits that are not part of the primary safety systems. For example, to add a safety mat or a light curtain one need simply plug it in to the one of the auxiliary disturbance circuits. The disturbance circuits monitor state changes only and do not use any software to detect a state change. Any detected state change will invoke an immediate stop of all motion of the patient positioner system.

An example of a disturbance that should invoke an immediate stop of all robot motion is a collision of the robot with any object. To facilitate rapid detection of any such collision, each of the arm segments preferably is covered with a cover that is spring loaded or otherwise implemented such that the cover is pushed in or deformed by any collision. Switches beneath the covers are positioned to be depressed by any such disturbance, and thereby to detect immediately a collision. The change of the switch state is detected immediately and an immediate stop of all movement invoked in response.

To facilitate use of a patient positioner system in accordance with the present invention a 3D emulator of the system in operation may be provided to operators thereof. As discussed above, the system may include 3D CAD representations of the robot and any attached devices. These representations may be used to generate a 3D graphical simulation of the motions to be performed by the system. Thus, a user will be able to first simulate the actions of the system and review them in a visually realistic manner prior to sending the commands to actually operate the system. Further, the emulator can be in constant communication with the robot controller to check for collisions real time.

A patient positioner system in accordance with the present invention preferably is implemented so as to allow for the use of standard industrial robot parts. In particular, the system is preferably implemented such that standard arm extension pieces can be attached easily to extend the radius of the work envelope.

Other aspects, objectives and advantages of the invention will become more apparent from the following detailed description when taken in conjunction with the accompanying drawings.

BRIEF DESCRIPTION OF THE DRAWINGS

The accompanying drawings incorporated in and forming a part of the specification illustrate several aspects of the present invention and, together with the description, serve to explain the principles of the invention. In the drawings.

While the invention will be described in connection with certain preferred embodiments, there is no intent to limit it to those embodiments. On the contrary, the intent is to cover all alternatives, modifications and equivalents as included within the spirit and scope of the invention as defined by the appended claims.

DETAILED DESCRIPTION OF THE INVENTION

The present invention will now be described in detail with reference to the particular application of a patient positioner system for use in positioning a human patient for radiotherapy treatment, such as in a proton beam treatment room or facility. It should be understood, however, the present invention may also have application in other types of treatments or other medical procedures, including diagnostic procedures and major surgery, for both humans and animals. Furthermore, it should be understood that features of the present invention may also find application entirely outside of the medical field, such as in an industrial, manufacturing, or scientific research setting.

Figure 1:
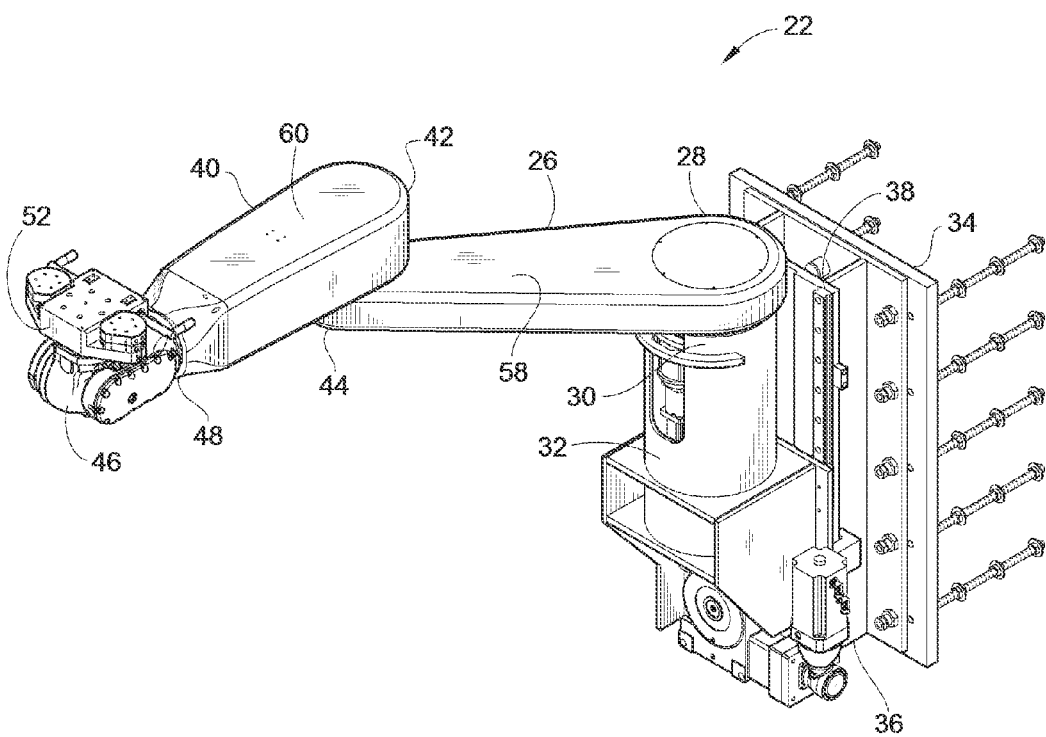
FIG. 1 is a perspective view illustration of an exemplary robot for a patient positioner system in accordance with the present invention.
Figure 2:
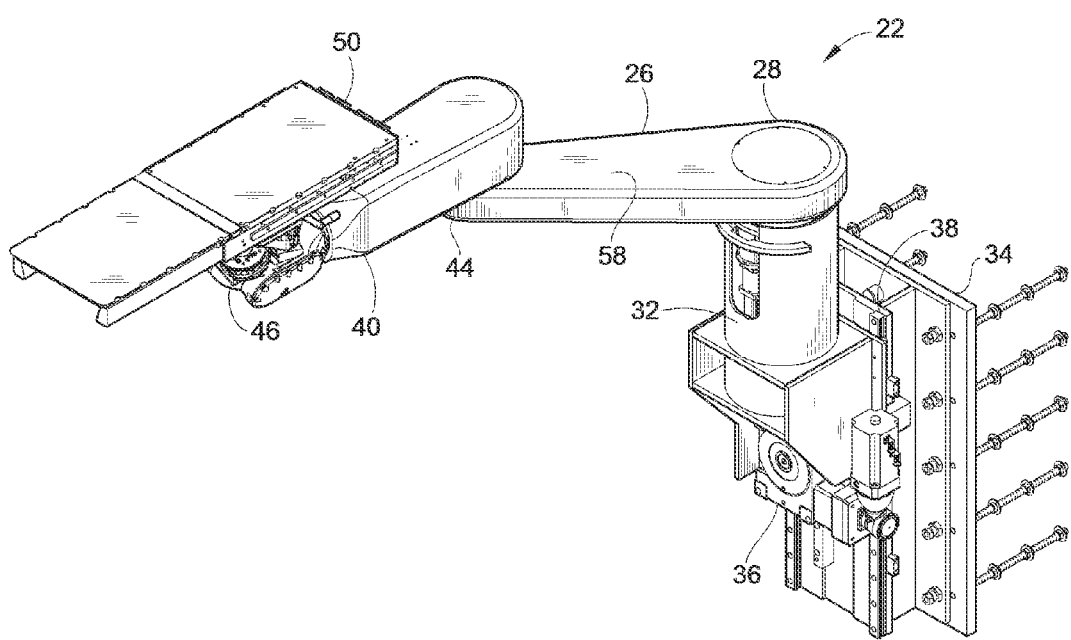
FIG. 2 is a perspective view illustration of an exemplary robot for a patient positioner system in accordance with the present invention with a patient table attached thereto and certain internal details revealed.

A complete patient positioner system 20 in accordance with the present invention includes a robot 22 (See FIG. 1) and a control system 24 (See FIG. 7) therefore. Unless otherwise described herein, conventional robot parts, assembly methods, hardware, software, safety and control circuitry as are known to those skilled in the art of industrial robots may be used to implement a robot 22 and control system 24 to implement the novel features and functions of a patient positioner system 20 in accordance with the present invention.

An exemplary robot 22 for a patient positioner system 20 in accordance with the present invention is illustrated in various views in FIGS. 1-4. The exemplary robot 22 provides five degrees of rotational freedom and a linear degree of freedom in the vertical direction. However, other robots having more degrees of freedom such as a six axis kinematic robot could be incorporated. The robot 22 includes a first arm segment 26 that is rotatably attached at a first end 28 thereof to the top 30 of a vertical shaft 32. The first robot arm segment 26 extends horizontally from the vertical shaft 32 and is rotatable in a complete circle in the horizontal direction about the vertical shaft 32.

The vertical shaft 32 is mounted for vertical movement to a mounting plate 34 or other mounting structure. In operation, the mounting plate 34 is secured to an appropriate building or other structure (not shown) below the floor level F (see FIG. 4) of the room in which the patient positioner system robot 22 is to operate. Sufficient room around the vertical shaft 32 must be provided in a pit underneath the floor F to allow for proper vertical movement of the shaft 32.

The vertical shaft 32 may be elevated and lowered via an appropriate motor driven mechanism 36. For example, a rack and pinion type system may provide the mechanism 36 for moving the shaft 32 vertically along a track 38 mounted to the mounting plate 34. Alternatively a traditional screw type mechanism may be employed.

A second robot arm segment 40 is moveably attached at a first end 42 thereof to the second end 44 of the first robot arm segment 26. The second robot arm segment 40 is preferably of the same length as the first robot arm segment 26 and is attached to the first arm segment 26 above the first arm segment 26 to extend parallel thereto such that the second arm segment 40 is rotatable in a complete circle in a horizontal direction about the joint between the arm segments, such that the second arm segment 40 passes over the first arm segment 26.

A robotic wrist assembly 46 is attached at the second end 48 of the second arm segment 40, extending generally upward therefrom so as not to interfere with rotation of the second arm segment 40 with respect to the first arm segment 26. A patient table 50 (see FIGS. 3-4), or other device, is attached to the wrist assembly 46. (As will be discussed in more detail below, the patient table 50, or other device, is preferably attached to the wrist assembly 46 via a novel dual coupler system 52 (see FIG. 1.).) The wrist assembly 46 provides for three axes of rotation (pitch, roll, and yaw) of the patient table 50 with respect to the second end 44 of the second arm segment 40.

Figure 3:
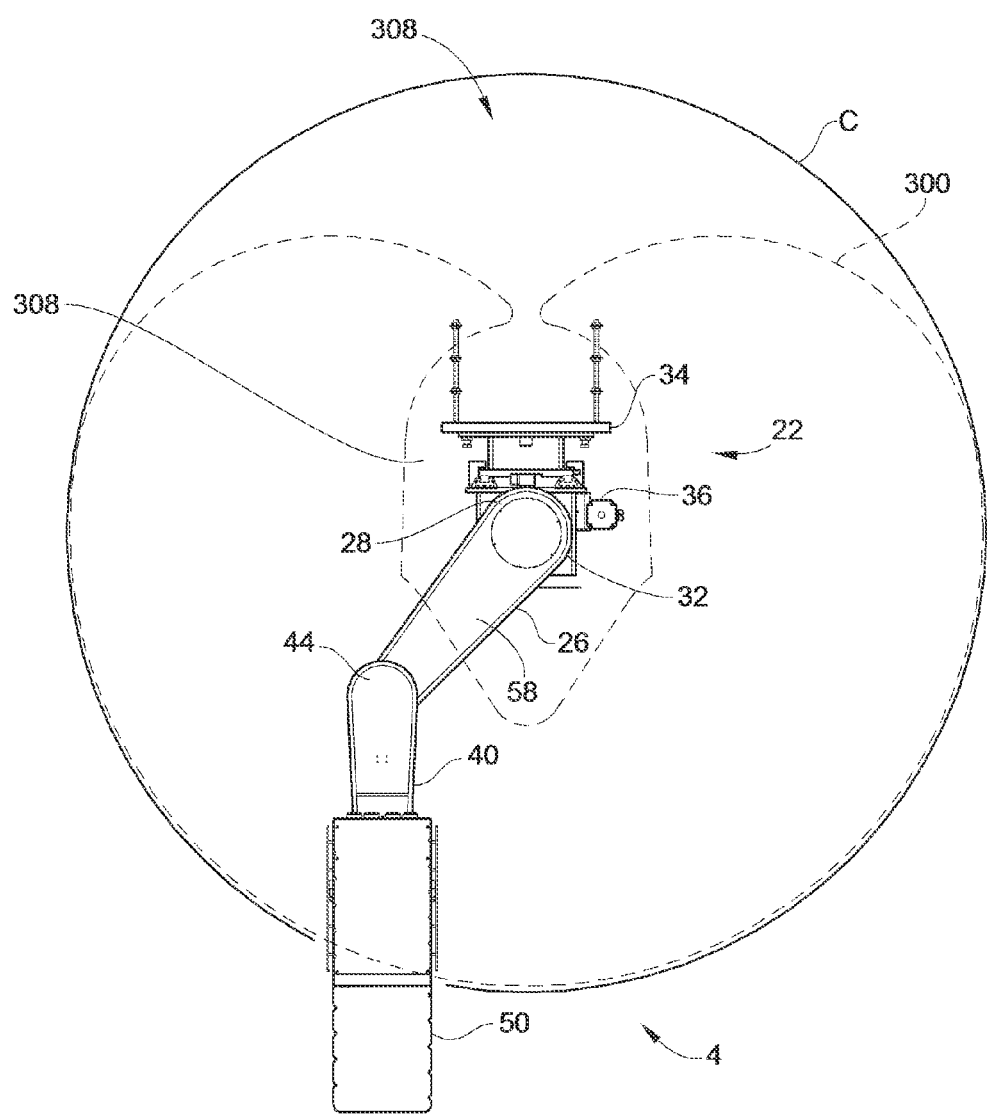
FIG. 3 is top plan view illustration of the exemplary robot for a patient positioner system and patient table of FIG. 2.
Figure 4:
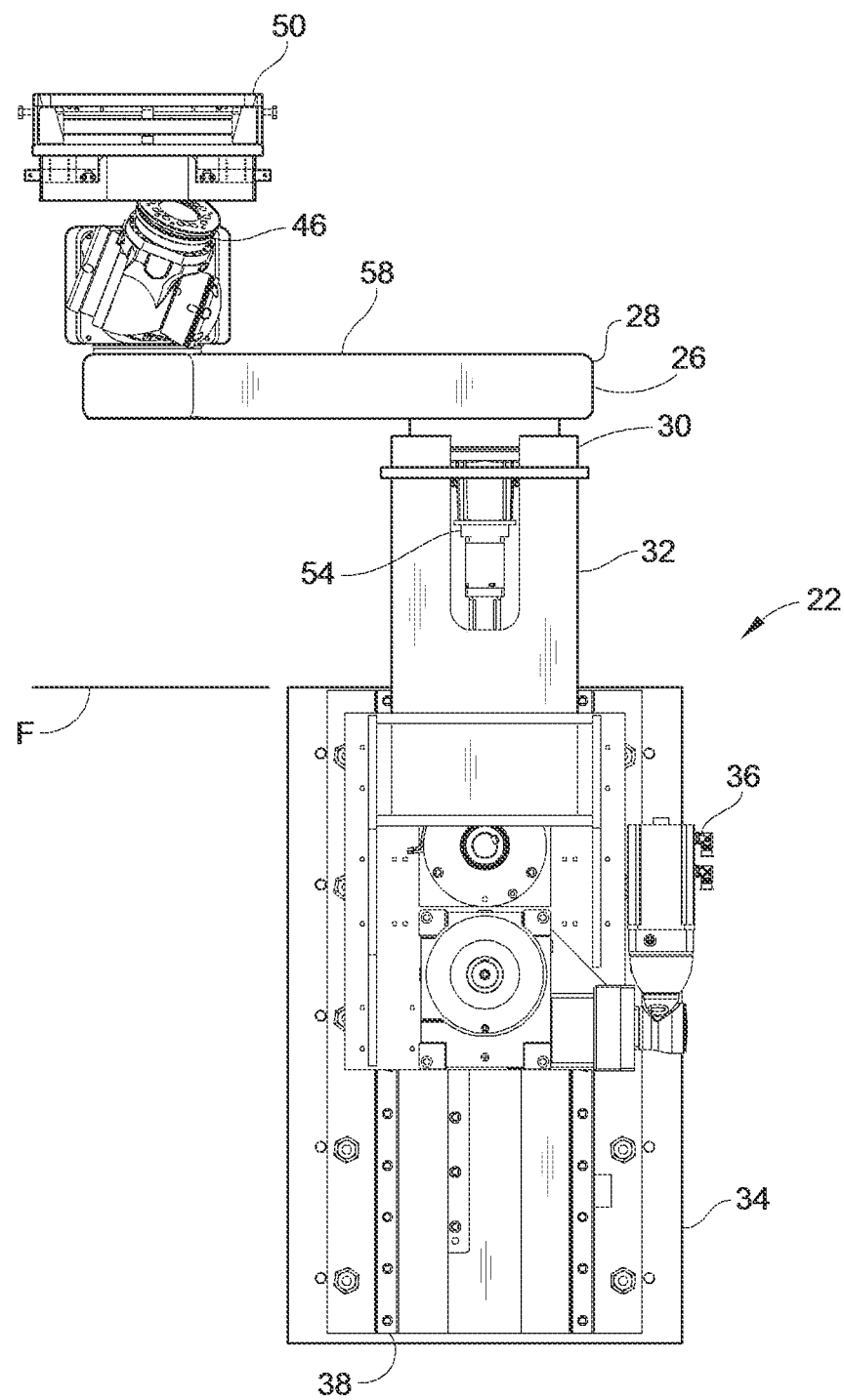
FIG. 4 is side plan view illustration of the exemplary robot for a patient positioner system and patient table of FIG. 2 as seen from the direction 4 of FIG. 3.
Figure 8:
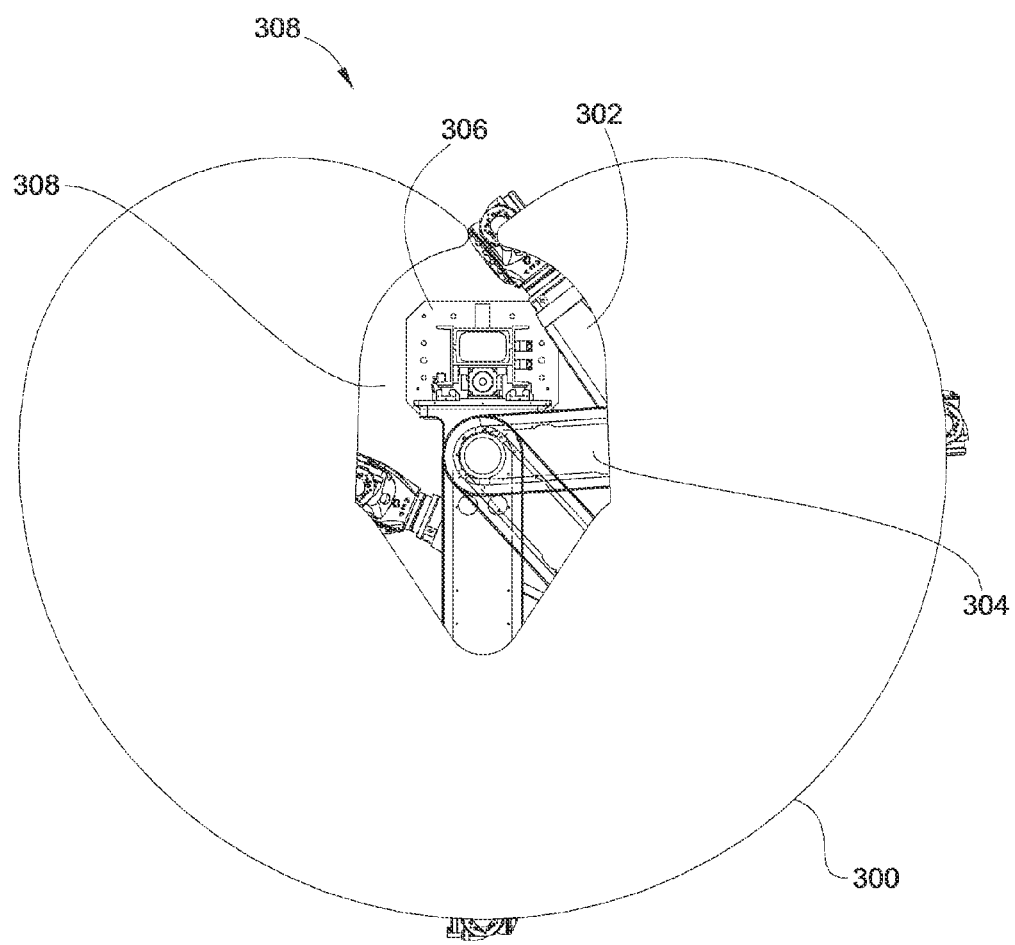
FIG. 8 is a representation of a prior art patient positioner system illustrating a reduced positioning envelope.

Due to the unique arrangement of the horizontal arm segments 26 and 40 and the vertical shaft 32 operating from the floor F a patient may be positioned anywhere in a complete envelope defined within circle C within the reach of the robot arm (see FIG. 3). Not only is the work envelope increased in size, but the arrangement of the robot arm segments 26 and 40 provides a more functional work envelope by allowing for the robot wrist 46 to reach any point in the envelope. This means that there are no "dead spots" in the envelope. The prior art envelope 300 illustrated in FIG. 8 is transposed over the envelope of the present invention to more clearly illustrate the difference in envelopes of the prior art and the present invention and the presence of dead spots 308. (The use of robot arm segments 26 and 40 of unequal length would result in such "dead spots".) It also allows for easy movement and collision free trajectories inside the work envelope. The easier motion trajectories allows for easy restrictions to the allowed envelope through standard firmware parameters. This is an advantage over previous robotic patient positioning systems in which the use of a vertical column to mount the system and the relative position of the robot arm segments (with the distal segment positioned below the proximal segment) reduces and restricts the available work envelope and freedom of arm movement trajectories. For example, imagining the vertical shaft 32 of FIG. 3 being mounted to a vertical column, in stead of beneath the floor, the available work envelope would be reduced, i.e. include dead spots 308 shown in FIGS. 3 and 8.

Figure 5:
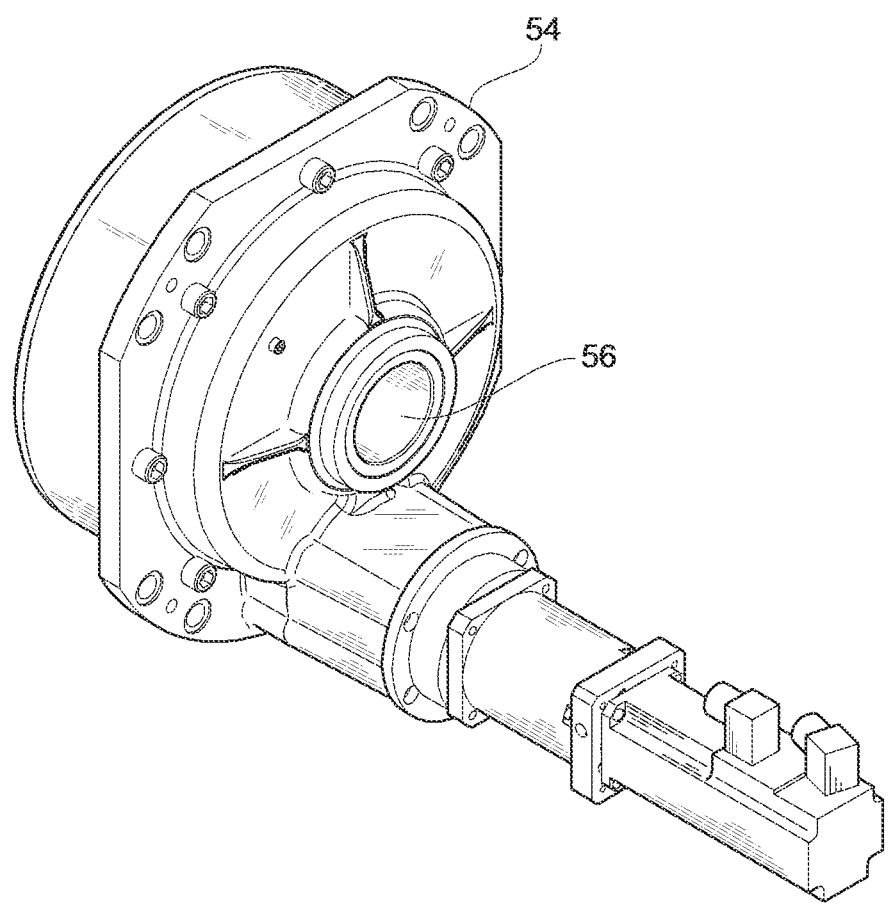
FIG. 5 is a perspective view illustration of an exemplary gear box for use in a robot for a patient positioner system in accordance with the present invention and having a through hole formed therethrough.

As in conventional industrial robots, appropriate servo or other motors and gear boxes are provided to implement highly controllable rotational movement at the junction between the vertical column 32 and the first arm segment 26, at the junction between the first 26 and second 44 arm segments, and in the robotic wrist assembly 46. In conventional robots, however, control cables and wires for the robot are run along the robot arms along the outside thereof. The result is hanging wires and cables that do not provide a neat appearance, which might be appreciated in a medical setting, and also may present safety and functionality issues. A patient positioner system 20 in accordance with the present invention preferably is designed to eliminate such wires, cables, and the like hanging from the robot arm segments. This improves the appearance, safety, and functionality of the system. To achieve this desired result the present invention preferably employs gear boxes 54, e.g., as illustrated in FIG. 5, connecting the first arm segment 26 to the vertical shaft 32 and between the first 26 and second 40 robot arm segments, that include through holes 56 or other apertures formed therein. This allows the necessary control cables to be run to the end of the second robot arm segment 40 through, rather than outside of, the gear boxes 54.

With the necessary control cables and wires running through the apertures 56 in the gear boxes 54, the arm segments 26 and 40 may be provided with covers, 58 and 60, respectively. With the control cables and wires contained entirely within the covers 58 and 60 along the length of the arm segments 26 and 40 a neat and sanitary appearance is provided and there is no risk of interference of hanging wires and cables with operation of the system.

The gear boxes 54 employed in the patient positioner system of the present invention preferably feature double gear reduction, to limit maximum rotation speed. This limits the speed of robot arm movement in the unlikely event of an out-of-control run away situation, thereby giving an operator an opportunity to hit an emergency stop switch to shut down the system.

Figure 6:
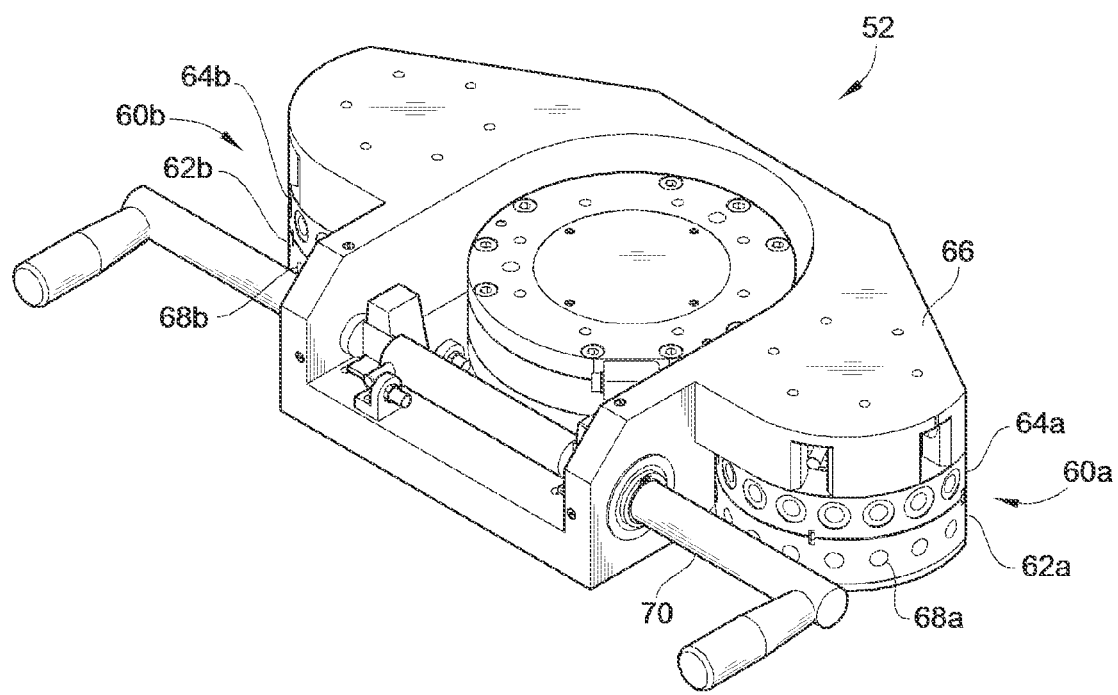
FIG. 6 is a perspective view illustration of an exemplary dual coupler system in accordance with the present invention.

An embodiment of the present invention preferably also features a uniquely designed dual coupler system that may be used to attach patient positioning devices (e.g., the patient table 50), quality assurance devices (e.g., test phantoms) and any other attachments, to the wrist end 46 of the robot system 24. An exemplary dual coupler system 52 in accordance with the present invention will now be described with reference to FIG. 6. (Note that the illustration of FIG. 6 is "upside down" with respect to FIG. 1.) Two independent couplers 60A and 6B are provided. Each coupler 60A and 60B is designed to, on its own, be sufficient to provide the safe and secure attachment required. Each coupler 60A and 60B is individually controlled through independent control circuits. This provides a double redundant safe coupling system. The dual coupler design allows for more space efficient implementation of the coupler system.

Each coupler system 60A and 60B includes a first coupler 62A and 62B that is secured to the patient table or other device to be attached to the robot 24. A second pair of couplers 64A and 64B are mounted to the wrist end 46 of the robot 24, e.g., via mounting plate structure 66. The first couplers 62A and 62B and second couplers 64A and 64B are designed to mate together. When joined together rods (not shown) extended into radial apertures 68A and 68B to join the couplers together. Control of the coupler pairs is completely independent. For additional safety a manually operated cam lever 70 may also preferably be provided to manually join the couplers together. Additionally, a mechanical safety clamp may be provided to assist the pneumatic coupler system.

Figure 7:
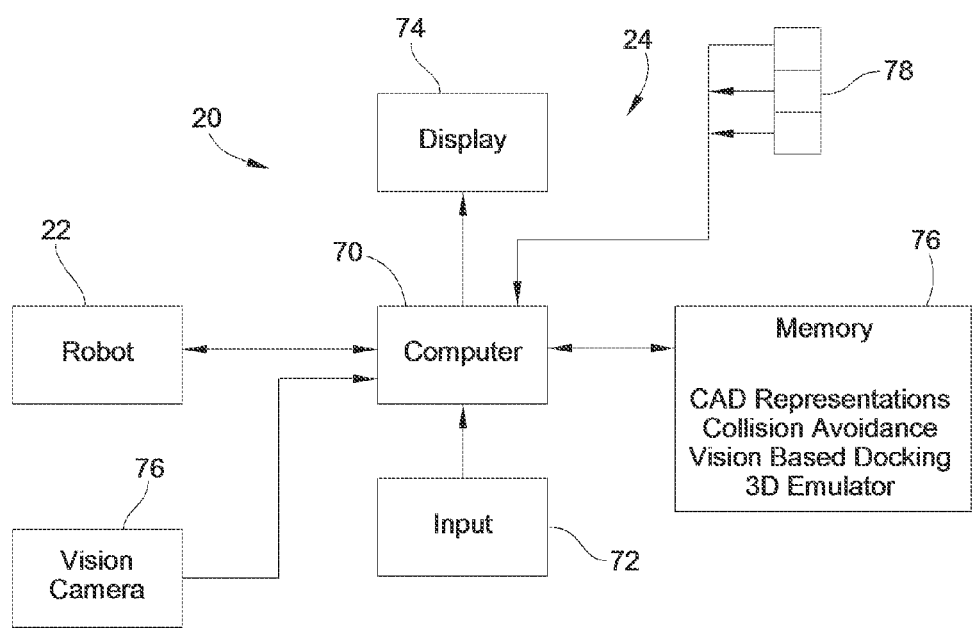
FIG. 7 is a schematic block diagram of a patient positioner system in accordance with the present invention showing a control system therefore.

An exemplary computer based control system 24 for a patient positioner system 20 in accordance with the present invention will now be described in more detail with reference to FIG. 7. It should be noted that known and conventional control and safety functionality and implementations as used in industrial and medical robot applications are not described herein.

The control system 24 in accordance with the present invention may be implemented using a conventional computer system 70 of the type conventionally used for industrial and/or medical robot control applications as appropriate. Such a computer system will include input devices 72, such as a keyboard, mouse, etc. and display or output devices 74 for interacting with the system control software in a conventional manner. The system control software may be implemented using conventional programming techniques and languages and stored in appropriate memory 76 associated with the computer system 70. In addition to conventional operating system and control software, a patient positioner system control system 24 may include additional data base information and program functionality implemented and stored in memory, such as computer aided design (CAD) representations of the robot 22 including any attached devices, collision avoidance algorithms that make use of such representations, software for implementing vision based docking in accordance with the present invention, and 3D emulation of robot operation, as will be discussed in more detail below.

The computer system 70 generates control signals that are provided (e.g., via appropriate driver and protection circuits) to control operation of the various motors that control movement of the robot 22. The computer system 70 also receives conventional signals from sensors or as feedback from that robot for improved system control and safety. For example, it is known for the computer system 70 to sense servo motor current levels as a safety measure.

In accordance with the present invention a load cell may preferably be positioned between the mating flange on a patient table 50, for example, and the robot flange. For example a six point piezoelectric strain gauge or similar structure may be used for this purpose. The output from such a device may be provided to the control computer 70 as a safety measure to detect forces at the end of the robot arm that may indicate, for example, that the patient position on the table is shifting, and there is a danger of a fall. Additionally, these structures may be used to haptic motion control based on force torque control of the device. Alternatively, such a structure may be used to determine patient weight or the like.

The patient positioning system 20 of the present invention features a device specific collision avoidance algorithm. As in conventional robot control systems, sensors are used to monitor the position in real space of specific points on the robot, e.g., the end of the robot arm near the wrist assembly. In addition to this positional feedback information for specific points on the robot, the present invention may employ computer aided design (CAD) representations of the entire robot structure surface, as well as of any device attached to the robot, e.g., a patient table, to determine the position in the work space of the surface of the entire system. Thus, the collision avoidance algorithm may be specific for each device attached to the patient positioner system. In this manner the robot may be operated so as to avoid collisions between any parts of the system itself, or between the system and any other structures where the position of such structures is provided to the system.

The present invention preferably employs a vision based docking system to facilitate the docking of different devices to the system. The docking system employs a vision camera 76 or other optical detection device mounted in an appropriate place in the treatment room within the work envelope of the robot 22, e.g., the camera 76 may be mounted in the floor of the treatment room. Devices to be mounted to the positioner system (e.g., patients already positioned on tables 50, test phantoms, etc.) are positioned on support carts in the room in the field of view of the camera 76. The support cart need only be in a certain approximate location for the camera to pick up the location of the device to be mounted on the system. Markings or other indices on the support cart are detected by the camera 76, thereby allowing the computer control system 24 to detect the position of the cart that carries the device considered for docking or un-docking. Bar code technology and alignment fiducial marks on the device and/or the cart allow the system 24 to identify the particular device to be attached to the robot 22 and to automatically manipulate the robot arm into the desired position to automatically attach the device to the robot 22, e.g. using the dual coupler system 52 described previously. This automated docking system increases the efficiency with which a treatment facility may be used, e.g., by reducing the time required to attach a patient to the system, and obviates the need for rigid docking fixtures in the floor of the treatment room.

As an additional safety feature, a patient positioner system in accordance with the present invention preferably is equipped with a plurality (e.g., three) auxiliary disturbance circuits 78. The auxiliary disturbance circuits 78 allow for the seamless addition of auxiliary disturbance switches and circuits that are not part of the primary safety systems. For example, to add a safety mat or a light curtain one need simply plug it in to the one of the auxiliary disturbance circuits 78. The disturbance circuits 78 monitor state changes only and do not use any software to detect a state change. Any detected state change will invoke an immediate stop of all motion of the patient positioner system 20.

An example of a disturbance that should invoke an immediate stop of all robot motion is a collision of the robot with any object. To facilitate rapid detection of any such collision, each of the arm segments 26 and 40 preferably is covered with a cover 58 and 60, respectively, that is spring loaded or otherwise implemented such that the cover 58 or 60 is pushed in or deformed by any collision. Switches beneath the covers are positioned to be depressed by any such disturbance, and thereby to detect immediately a collision. The change of the switch state is detected immediately and an immediate stop of all movement invoked in response.

To facilitate use of a patient positioner system 20 in accordance with the present invention a 3D emulator of the system in operation may be provided to operators thereof via the control system 24. As discussed above, the control system 24 may include 3D CAD representations of the robot 22 and any attached devices. These representations may be used to generate a 3D graphical simulation of the motions to be performed by the system. Thus, a user will be able to first simulate the actions of the system and review them in a visually realistic manner on the computer display 74 prior to sending the commands to actually operate the robot 22.

All references, including publications, patent applications, and patents cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) is to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A control system for a patient positioner system that includes a robot having a horizontally rotatable first arm segment, a horizontally rotatable second arm segment coupled to the first arm segment, and a wrist assembly coupled to the second arm segment, and a patient table attached to the wrist assembly of the robot, the control system being configured to control the robot to position the patient table at all points within a complete circular envelope defined by a maximum reach of the first and second arm segments without any dead spots, comprising:
   at least one force sensor coupled to at least one of the robot or the patient table whereby the at least one force sensor generates a control input from a user directly applying a load to at least one of the robotic arm or the patient table to which the force sensor is coupled;
   at least one position sensor coupled to at least one of the robot or the patient table whereby the at least one position sensor generates position information of at least one specific point on the robot or patient table in real space; and
   an optical detection device to monitor location of devices to be coupled to the robotic arm; and
   an electronic controller operatively coupled to the at least one force sensor, the at least one position sensor, and the optical detection device, the electronic controller programmed to control the robot to position the patient table in response to the control input provided by the at least one force sensor, the controller further including a collision avoidance algorithm and a computer aided design representations of the robot and the patient table, the collision avoidance algorithm using the computer aided design representations to determine a work space for the entire system, the controller further including a vision based docking system to position the robot to dock with the devices based on a visual position thereof.

2. The control system of claim 1, further comprising a plurality of auxiliary disturbance circuits, the auxiliary disturbance circuits configured to effectuate immediate stopping of all motion of the robot and the patient table upon a detected state change of any external auxiliary disturbance system coupled thereto.

3. The control system of claim 2, further comprising a light curtain coupled to the auxiliary disturbance circuit, and wherein the light curtain provides the state change to the disturbance circuit upon any penetration the light curtain by an object.

4. A patient positioner system, comprising:
   a robot having a first arm segment, a second arm segment coupled to the first arm segment, and a wrist assembly coupled to the second arm segment;
   a patient table attached to the wrist assembly;
   a control system operably coupled to the robot, wherein the control system is configured to control the robot to vary a position of the patient table, including a vertical position of the table, at all points within a complete circular envelope wherein the complete circular envelope is defined by a maximum reach of the first and second arm segments without any dead spots, wherein the control system has a 3D emulator that provides 3D simulation of motions being commanded such that a user can simulate the actions of the patient table.

5. The patient positioner system according to claim 4, wherein the control system further includes mechanical axis range monitoring that monitors the parameters of the motion of the robot about the various axes to monitor the movement of the robot and the patient table to maintain the movement within predefined limits.

6. The patient positioner system according to claim 4, wherein the control system includes at least one force sensor coupled to at least one of the robot or the patient table whereby the control system receives a control input from a user directly applying a load to at least one of the robotic arm or the patient table to which the force sensor is coupled, and wherein the control system controls the robot to position the patient table in response thereto.

7. The patient positioner system according to claim 4, wherein the wrist assembly includes a mechanical restriction on a degree of motion along pitch and roll axes of rotation out of the horizontal plane.

8. The patient positioner system according to claim 7, wherein the mechanical restriction prevents rotation out of the horizontal plane of a degree greater than 15 degrees in either direction about both the pitch and roll axes.

9. The patient positioner system according to claim 4, wherein the control system includes at least one position sensor coupled to at least one of the robot or the patient table whereby the control system receives position information of at least one specific point on the robot or patient table in real space, the control system further including a collision avoidance algorithm.

10. The patient positioner system according to claim 9, wherein the control system is programmed with computer aided design representations of the robot and the patient table, the collision avoidance algorithm using the computer aided design representations to determine a work space for the entire system.

11. The patient positioner system according to claim 4, wherein the control system includes an optical detection device to monitor location of devices to be coupled to the robotic arm, the control system further including a vision based docking system to position the robot to dock with the devices based on a visual position thereof.

12. The patient positioner system according to claim 4, wherein the control system includes a plurality of auxiliary disturbance circuits, the auxiliary disturbance circuits being operably couplable to auxiliary disturbance systems that are not part of any primary safety system of the robotic arm, and wherein the auxiliary disturbance circuits are operably configured to effectuate immediate stopping of all motion of the robot and the patient table upon a detected state change of any of the auxiliary disturbance systems.

13. The patient positioner system according to claim 12, wherein the auxiliary disturbance circuits monitor state changes only and do not use any software to detect the state change, and wherein the auxiliary disturbance circuits invoke an immediate stop of all motion of the robot and the patient table upon any detected state change.

14. The patient positioner system according to claim 12, wherein the auxiliary disturbance system includes a cover for at least one of the robot or the patient table that is configured to detect a collision with an object and provide the detected state change to the auxiliary disturbance circuit to immediately stop all motion of the robot and the patient table.

15. A patient positioner system, comprising:
a robot having a first arm segment, a second arm segment coupled to the first arm segment, and a wrist assembly coupled to the second arm segment;
a patient table attached to the wrist assembly; wherein the patent table is configured with a dual coupler system that includes two independent couplers, each independent coupler being sufficient to provide safe and secure attachment of the patient table to provide redundant coupling of the patient table to the wrist assembly;
a control system operably coupled to the robot, wherein the control system is configured to control the robot to vary a position of the patient table, including the vertical position of the table, at all points within a complete circular envelope wherein the complete circular envelope is defined by a maximum reach of the first and second arm segments without any dead spots.

16. The patient positioner system according to claim 15 wherein each of the independent couplers of the dual coupler system further includes independent control circuits for control thereof.

17. The patient positioner system according to claim 15 wherein the control system includes at least one force sensor coupled to at least one of the robot or the patient table whereby the control system receives a control input from a user directly applying a load to at least one of the robotic arm or the patient table to which the force sensor is coupled, and wherein the control system controls the robot to position the patient table in response thereto.

18. The patient positioner system according to claim 15, wherein the control system includes at least one force sensor coupled to at least one of the robot or the patient table whereby the control system receives a control input from a user directly applying a load to at least one of the robotic arm or the patient table to which the force sensor is coupled, and wherein the control system controls the robot to position the patient table in response thereto.

19. The patient positioner system according to claim 15, wherein the wrist assembly includes a mechanical restriction on a degree of motion along pitch and roll axes of rotation out of the horizontal plane.

20. The patient positioner system according to claim 19, wherein the mechanical restriction prevents rotation out of the horizontal plane of a degree greater than 15 degrees in either direction about both the pitch and roll axes.

21. The patient positioner system according to claim 15, wherein the control system includes at least one position sensor coupled to at least one of the robot or the patient table whereby the control system receives position information of at least one specific point on the robot or patient table in real space, the control system further including a collision avoidance algorithm.

22. The patient positioner system according to claim 21, wherein the control system is programmed with computer aided design representations of the robot and the patient table, the collision avoidance algorithm using the computer aided design representations to determine a work space for the entire system.

23. The patient positioner system according to claim 15, wherein the control system includes an optical detection device to monitor location of devices to be coupled to the robotic arm, the control system further including a vision based docking system to position the robot to dock with the devices based on a visual position thereof.

24. The patient positioner system according to claim 15, wherein the control system includes a plurality of auxiliary disturbance circuits, the auxiliary disturbance circuits being operably couplable to auxiliary disturbance systems that are not part of any primary safety system of the robotic arm, and wherein the auxiliary disturbance circuits are operably configured to effectuate immediate stopping of all motion of the robot and the patient table upon a detected state change of any of the auxiliary disturbance systems.

25. The patient positioner system according to claim 24, wherein the auxiliary disturbance circuits monitor state changes only and do not use any software to detect the state change, and wherein the auxiliary disturbance circuits invoke an immediate stop of all motion of the robot and the patient table upon any detected state change.

26. The patient positioner system according to claim 24, wherein the auxiliary disturbance system includes a cover for at least one of the robot or the patient table that is configured to detect a collision with an object and provide the detected state change to the auxiliary disturbance circuit to immediately stop all motion of the robot and the patient table.

* * * * *